(12) United States Patent
Rao et al.

(10) Patent No.: US 8,506,647 B2
(45) Date of Patent: Aug. 13, 2013

(54) SYSTEM FOR MAINTAINING BODY CANAL PATENCY

(75) Inventors: Doreen S. Rao, Watertown, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 872 days.

(21) Appl. No.: 10/075,144

(22) Filed: Feb. 14, 2002

(65) Prior Publication Data

US 2003/0153970 A1 Aug. 14, 2003

(51) Int. Cl.
*A61F 2/04* (2006.01)

(52) U.S. Cl.
USPC ........................................... 623/23.65

(58) Field of Classification Search
USPC ............. 623/23.64, 23.66, 23.7, 1.15, 1.16, 623/23.65; 604/907; 606/108, 191; 24/3.3, 24/3.13, 49.1, 56, 58; 63/4, 38, 12, 13; 70/457; 59/80, 82, 84, 93, 95; D8/499; D11/13
See application file for complete search history.

(56) References Cited

U.S. PATENT DOCUMENTS

| | | | | |
|---|---|---|---|---|
| 2,274,269 A | * | 2/1942 | Jellinek | 63/1.17 |
| D175,510 S | * | 9/1955 | Katz | D11/8 |
| 2,739,596 A | * | 3/1956 | Roberts | 606/188 |
| 3,789,828 A | | 2/1974 | Schulte | |
| 3,938,529 A | | 2/1976 | Gibbons | |
| 3,977,408 A | | 8/1976 | MacKew | |
| 3,985,601 A | | 10/1976 | Panagrossi | |
| 4,026,296 A | | 5/1977 | Stoy et al. | |
| 4,026,298 A | | 5/1977 | Grausz | |
| 4,043,346 A | | 8/1977 | Mobley et al. | |
| 4,095,587 A | * | 6/1978 | Ishikawa | 600/15 |
| 4,151,840 A | | 5/1979 | Barrington | |
| 4,194,509 A | | 3/1980 | Pickering et al. | |
| 4,212,304 A | | 7/1980 | Finney | |
| 4,225,979 A | | 10/1980 | Rey et al. | |
| 4,259,850 A | * | 4/1981 | Lalieu | 63/13 |
| 4,284,081 A | | 8/1981 | Kasper et al. | |
| 4,294,260 A | * | 10/1981 | Veatch | 600/431 |
| 4,307,582 A | * | 12/1981 | Mancini | 63/12 |
| 4,307,723 A | | 12/1981 | Finney | |
| 4,334,327 A | * | 6/1982 | Lyman et al. | 623/23.66 |
| D265,894 S | * | 8/1982 | Barr | D11/43 |
| 4,531,933 A | | 7/1985 | Norton et al. | |
| 4,543,695 A | * | 10/1985 | Dorsey | 24/662 |
| 4,579,554 A | | 4/1986 | Glassman | |

(Continued)

OTHER PUBLICATIONS

Collier et al., "Proximal Stent Displacement as Complication of Pigtail Ureteral Stent," Urology, Apr. 1979, vol. XIII, No. 4, pp. 372-375.

(Continued)

*Primary Examiner* — Thomas McEvoy (57) ABSTRACT

A device is provided for insertion and implantation in a patient's bodily canals or vessels such as the ureter. The device includes interconnected loops that form a flexible structure that may span the length of a bodily canal. The device may include retaining elements at both or either ends. Further according to the present invention, there is provided a stylet for delivering the device to the desired body canal. The device minimizes contact with the lining of the bodily canal while retaining the patency of the canal. The device also is adjustable in length and shape. It is particularly useful for maintaining the tortousness of a body canal.

48 Claims, 8 Drawing Sheets

(56) References Cited

U.S. PATENT DOCUMENTS

| | | |
|---|---|---|
| 4,610,657 A | 9/1986 | Densow |
| 4,643,716 A | 2/1987 | Drach |
| 4,643,720 A | 2/1987 | Lanciano |
| 4,655,777 A | 4/1987 | Dunn et al. |
| 4,671,795 A | 6/1987 | Mulchin |
| 4,713,049 A | 12/1987 | Carter |
| 4,785,059 A | 11/1988 | Fydelor et al. |
| 4,787,884 A | 11/1988 | Goldberg |
| 4,790,809 A | 12/1988 | Kuntz |
| 4,790,810 A | 12/1988 | Pugh, Jr. et al. |
| 4,813,925 A | 3/1989 | Anderson, Jr. et al. |
| 4,813,935 A | 3/1989 | Haber et al. |
| 4,820,262 A | 4/1989 | Finney |
| 4,822,333 A | 4/1989 | Lavarenne |
| 4,856,516 A | 8/1989 | Hillstead |
| 4,861,658 A * | 8/1989 | Griffin et al. ................ 428/336 |
| 4,874,360 A | 10/1989 | Goldberg et al. |
| 4,878,906 A | 11/1989 | Lindemann et al. |
| 4,893,623 A | 1/1990 | Rosenbluth |
| 4,913,683 A | 4/1990 | Gregory |
| 4,932,938 A | 6/1990 | Goldberg et al. |
| 4,932,956 A | 6/1990 | Reddy et al. |
| 4,950,228 A | 8/1990 | Knapp, Jr. et al. |
| 4,954,126 A | 9/1990 | Wallstén |
| 4,955,859 A | 9/1990 | Zilber |
| 4,957,479 A | 9/1990 | Roemer |
| 4,963,129 A | 10/1990 | Rusch |
| 4,990,133 A | 2/1991 | Solazzo |
| 5,007,898 A | 4/1991 | Rosenbluth et al. |
| 5,019,102 A | 5/1991 | Hoene |
| 5,026,377 A | 6/1991 | Burton et al. |
| 5,041,085 A | 8/1991 | Osborne et al. |
| 5,059,169 A | 10/1991 | Zilber |
| 5,061,275 A | 10/1991 | Wallstén et al. |
| 5,078,684 A | 1/1992 | Yasuda |
| 5,078,720 A | 1/1992 | Burton et al. |
| 5,085,664 A | 2/1992 | Bozzo |
| 5,096,454 A | 3/1992 | Sample |
| 5,097,848 A | 3/1992 | Schwarz |
| 5,116,309 A | 5/1992 | Coll |
| 5,116,365 A | 5/1992 | Hillstead |
| 5,135,536 A | 8/1992 | Hillstead |
| 5,141,502 A | 8/1992 | Macaluso, Jr. |
| 5,147,370 A | 9/1992 | McNamara et al. |
| 5,176,625 A | 1/1993 | Brison |
| 5,176,664 A | 1/1993 | Weisman |
| D335,106 S * | 4/1993 | Teeter ......................... D11/202 |
| 5,209,239 A * | 5/1993 | Watanabe et al. ............. 600/587 |
| 5,221,253 A | 6/1993 | Coll |
| 5,224,953 A | 7/1993 | Morgentaler |
| 5,246,445 A | 9/1993 | Yachia et al. |
| 5,253,366 A * | 10/1993 | Marlo et al. ......................... 2/145 |
| 5,269,802 A | 12/1993 | Garber |
| 5,282,472 A | 2/1994 | Companion et al. |
| 5,282,784 A | 2/1994 | Willard |
| 5,289,831 A | 3/1994 | Bosley |
| 5,344,435 A | 9/1994 | Turner et al. |
| 5,346,467 A | 9/1994 | Coll |
| 5,352,198 A | 10/1994 | Goldenberg et al. |
| 5,354,263 A | 10/1994 | Coll |
| 5,354,309 A | 10/1994 | Schnepp-Pesch et al. |
| 5,356,423 A | 10/1994 | Tihon et al. |
| 5,364,340 A | 11/1994 | Coll |
| 5,372,600 A | 12/1994 | Beyar et al. |
| 5,383,892 A | 1/1995 | Cardon et al. |
| 5,401,257 A | 3/1995 | Chevalier, Jr. et al. |
| 5,419,764 A | 5/1995 | Roll |
| 5,421,955 A | 6/1995 | Lau et al. |
| 5,433,723 A | 7/1995 | Lindenberg et al. |
| 5,449,373 A | 9/1995 | Pinchasik et al. |
| 5,466,242 A | 11/1995 | Mori |
| 5,490,521 A | 2/1996 | Davis et al. |
| 5,507,769 A | 4/1996 | Marin et al. |
| 5,514,176 A | 5/1996 | Bosley, Jr. |
| 5,514,178 A | 5/1996 | Torchio |
| 5,520,664 A | 5/1996 | Bricault, Jr. et al. |
| 5,520,697 A | 5/1996 | Lindenberg et al. |
| 5,523,092 A | 6/1996 | Hanson et al. |
| 5,525,388 A | 6/1996 | Wand et al. |
| 5,527,281 A | 6/1996 | Haas |
| 5,527,532 A | 6/1996 | Edelman et al. |
| 5,531,741 A | 7/1996 | Barbacci |
| 5,540,713 A | 7/1996 | Schnepp-Pesch et al. |
| 5,554,147 A | 9/1996 | Batich et al. |
| 5,569,219 A | 10/1996 | Hakki et al. |
| 5,599,291 A | 2/1997 | Balbierz et al. |
| 5,607,417 A | 3/1997 | Batich et al. |
| 5,619,875 A * | 4/1997 | Lahaussois ...................... 70/457 |
| 5,632,163 A * | 5/1997 | Inoue ................................ 63/12 |
| 5,634,878 A | 6/1997 | Grundei et al. |
| 5,647,843 A | 7/1997 | Mesrobian et al. |
| 5,667,486 A | 9/1997 | Mikulich et al. |
| 5,669,239 A * | 9/1997 | Tobita ................................ 63/12 |
| 5,674,241 A | 10/1997 | Bley et al. |
| 5,681,274 A | 10/1997 | Perkins et al. |
| 5,695,517 A | 12/1997 | Marin et al. |
| 5,707,386 A | 1/1998 | Schnepp-Pesch et al. |
| 5,709,874 A | 1/1998 | Hanson et al. |
| 5,711,314 A | 1/1998 | Ardito |
| 5,716,981 A | 2/1998 | Hunter et al. |
| 5,746,723 A | 5/1998 | Freeman et al. |
| 5,752,971 A | 5/1998 | Rosenbluth et al. |
| 5,766,209 A | 6/1998 | Devonec |
| 5,769,818 A | 6/1998 | El Maoued |
| 5,776,161 A | 7/1998 | Globerman |
| 5,782,742 A | 7/1998 | Crocker et al. |
| 5,782,838 A | 7/1998 | Beyar et al. |
| 5,788,687 A | 8/1998 | Batich et al. |
| 5,792,400 A | 8/1998 | Talja et al. |
| 5,794,459 A * | 8/1998 | Ignatowski ........................ 63/38 |
| 5,824,037 A | 10/1998 | Fogarty et al. |
| 5,843,117 A | 12/1998 | Alt et al. |
| 5,871,475 A | 2/1999 | Frassica |
| 5,876,417 A | 3/1999 | Devonec et al. |
| 5,886,026 A | 3/1999 | Hunter et al. |
| 5,902,254 A * | 5/1999 | Magram ......................... 600/585 |
| 5,902,283 A | 5/1999 | Darouiche et al. |
| 5,906,575 A | 5/1999 | Conway et al. |
| 5,911,732 A | 6/1999 | Hojeibane |
| 5,914,345 A | 6/1999 | Slepian et al. |
| 5,916,195 A | 6/1999 | Eshel et al. |
| 5,921,952 A | 7/1999 | Desmond, III et al. |
| 5,931,860 A | 8/1999 | Reid et al. |
| 5,935,094 A | 8/1999 | Zupkas |
| 5,938,682 A | 8/1999 | Hojeibane et al. |
| 5,964,744 A | 10/1999 | Balbierz et al. |
| 5,971,967 A | 10/1999 | Willard |
| 5,980,553 A | 11/1999 | Gray et al. |
| 5,985,307 A | 11/1999 | Hanson et al. |
| 5,989,230 A | 11/1999 | Frassica |
| 5,994,341 A | 11/1999 | Hunter et al. |
| 6,004,348 A | 12/1999 | Banas et al. |
| 6,013,854 A | 1/2000 | Moriuchi |
| 6,017,363 A | 1/2000 | Hojeibane |
| 6,019,779 A | 2/2000 | Thorud et al. |
| 6,026,515 A * | 2/2000 | Nielson et al. ...................... 2/244 |
| 6,033,413 A | 3/2000 | Mikus et al. |
| 6,042,577 A | 3/2000 | Chu et al. |
| 6,056,775 A | 5/2000 | Borghi et al. |
| 6,059,808 A | 5/2000 | Boussignac et al. |
| 6,063,113 A | 5/2000 | Kavteladze et al. |
| 6,066,168 A | 5/2000 | Lau et al. |
| 6,069,135 A | 5/2000 | Falk et al. |
| 6,070,434 A * | 6/2000 | Traver ........................... 63/1.11 |
| 6,087,552 A | 7/2000 | Gregory |
| 6,097,978 A | 8/2000 | Demarais et al. |
| 6,098,250 A * | 8/2000 | Katz ........................... 24/16 PB |
| 6,105,392 A * | 8/2000 | Biagi ................................ 63/12 |

| | | | |
|---|---|---|---|
| 6,110,198 A | 8/2000 | Fogarty et al. | |
| 6,110,212 A | 8/2000 | Gregory | |
| 6,123,722 A | 9/2000 | Fogarty et al. | |
| 6,129,756 A | 10/2000 | Kugler et al. | |
| 6,159,237 A | 12/2000 | Alt et al. | |
| 6,162,243 A | 12/2000 | Gray et al. | |
| 6,174,305 B1 | 1/2001 | Mikus et al. | |
| 6,176,821 B1 | 1/2001 | Crocker et al. | |
| 6,193,745 B1 | 2/2001 | Fogarty et al. | |
| 6,214,037 B1* | 4/2001 | Mitchell et al. | 623/1.11 |
| 6,238,368 B1 | 5/2001 | Devonec | |
| 6,258,117 B1* | 7/2001 | Camrud et al. | 623/1.16 |
| 6,290,666 B1 | 9/2001 | Devonec | |
| 6,338,345 B1 | 1/2002 | Johnson et al. | |
| 6,458,119 B1* | 10/2002 | Berenstein et al. | 606/151 |
| 2001/0044254 A1* | 11/2001 | Gardner | 446/268 |

OTHER PUBLICATIONS

Kwok et al., "Design of infection-resistant antibiotic-releasing polymers," Journal of Controlled Release, Apr. 1999, vol. 62, pp. 301-311.

Pugach et al., "Antibiotic Hydrogel Coated Foley Catheters for Prevention of Urinary Tract Infection in a Rabbit Model" The Journal of Urology, Sep. 1999, vol. 162, pp. 883-887.

Hepperlen et al., "Self-Retained Internal Ureteral Stents: A New Approach," The Journal of Urology, Jun. 1978, vol. 119, pp. 731-734.

Mardis et al., "Polyethylene Double-Pigtail Ureteral Stents," Urologic Clinics of North America, Feb. 1982, vol. 9, No. 1 pp. 95-101.

* cited by examiner

FIG. 9E

SYSTEM FOR MAINTAINING BODY CANAL PATENCY

TECHNICAL FIELD

The invention generally involves devices, such as stents, that are useful for maintaining the patency of a body canal, their delivery systems, and related uses.

BACKGROUND INFORMATION

The ureter is a fibromuscular tube that conveys urine from the kidney to the bladder. The ureter begins with the renal pelvis and enters the bladder at an area called the trigone. The bladder trigone is the triangulated area between both ureteral orifices and the bladder neck. A normal length for an adult ureter is approximately 16 to 18 inches.

Ureteral stenosis, stones in the ureter, and other medical conditions call for the use of a ureteral stent or prosthesis. Currently available types of indwelling ureteral stents are variations of the same basic tube structure. The outer and inner diameter, and the size of the drainage holes or the retention elements that are to be placed in the kidney and bladder vary among the known stent types. None of the known ureteral stents adequately address the pain generally associated with an indwelling ureteral stent.

Ureteral pain associated with a stent is thought to arise from the following: 1) contact between the stent and the mucosal lining of the ureter, or, especially, with the bladder trigone; 2) flank pain from vesico-ureteral reflux which occurs primarily during voiding; and 3) irritation caused by the stent in the intramural tunnel of the urinary bladder wall which is 1-2 cm proximal to the ureteral orifice.

After an invasive surgical procedure to remove a kidney stone from a patient's ureter, the lining of the ureteral lumen tends to be swollen and inflamed. Post-surgical stent placement, therefore, poses a particular challenge in terms of patient comfort.

Pain and discomfort associated with indwelling stents or prostheses is not unique to the ureter. Other body canals, for example, blood vessels such as the coronary vessels, and bile ducts, can also benefit from a new stent design that alleviates the pain associated with stents while maintaining the patency of the body canal.

In addition, an interventional device such as a stent that can better accommodate the anatomy of body canals is needed. Such a device would not only conform to the shape and length of a body canal, the device would also adjust, preferably automatically, to changes in the shape and length of the body canal that occur, for example, during normal bodily functions.

SUMMARY OF THE INVENTION

It is an objective of the invention to provide a patient, male or female, with a flexible device designed to maintain the patency of a body canal while minimizing the pains and discomfort commonly associated with an indwelling device. Such body canals include and are not limited to the ureter, the urethra, the bile duct, the esophagus, the intestine, the colon, and blood vessels.

The invention achieves its objectives by minimizing mucosal contact between an interventional device and a targeted body canal and preserving the natural tortuousness of the body canal. For example, by keeping the ureter in its natural tortuous state after implanting an embodiment of the invention, ureteral reflux is effectively prevented during voiding. Specifically, the invention provides an elongated device that include a plurality of discrete loops linked through multiple flexible connections where the loop members can move in multiple directions in relation to another.

The invention provides an interventional device that has an end-piece at each end and an elongated body portion in between. The body portion has multiple interconnected loops that are sized to fit within the targeted body canal. Each loop is made of a member that defines at least one opening. And each loop is linked to at least another loop through passing its member through at least one opening in another loop. In a particular embodiment, at least one loop member passes through the openings of at least two other loops. In another embodiment, at least one loop member passes through one or two loop openings.

The loops in the device according to the invention minimize mucosal contact with the body canal. The flexible connections between the loops also allow the elongated body portion to conform to the anatomy of a body canal without compromising the tortuousness of the body canal. Additional flexibility in conforming to the anatomy of a body canal may result from using a radially compressible material for at least part of the body portion. Also because of the flexible connections between the loops, the longitudinal length of the body portion is adjustable, i.e., the body portion is axially compressible. The loops may assume various shapes and structures.

The body portion may further include a non-loop segment such as a tubular segment. Preferably, the non-loop element has an uneven surface that may help prevent stenosis after the device is implanted in a body canal. The non-loop element may further be made of a radially compressible material.

The end-pieces may serve as a retention device. In a particular embodiment, an end piece is substantially spherical and prevents migration of the interventional device once properly positioned.

In another embodiment of the invention, a drug-dispenser is associated with the device of the invention. The drug-dispenser may be a drug-releasing plug or disk, or a coating on at least a portion of the device.

Another aspect of the invention relates to a delivery assembly that can be used to deliver an interventional device to a target site in the body. According to this aspect of the invention, a stylet is reversibly attached to a proximal end-piece of the interventional device and lends sufficient rigidity to the device that once the stylet is pushed up a body canal, it advances the interventional device along with it. In one embodiment where the stylet is used to deliver the interventional device of the invention, the stylet is free of the body portion and the distal end-piece of the device. In one embodiment, the stylet is reversibly attached to the proximal end-piece of the interventional device through a luer linkage. In another embodiment, the proximal end of the stylet is a male-cot which assists in the attachment of the stylet to the proximal end-piece of the device of the invention.

Embodiments of the invention may include additional features. For instance, a retrieval suture may be attached to the distal end-piece of the interventional device of the invention to assist the removal of the device from the body. The device of the invention may also be made of a biodegradable material, eliminating the need for removal. The device may further include a radiopaque marker. The device may be made of a biocompatible material such as a polymeric material or a metal.

A method is provided for retaining body canal patency in a patient, which comprises inserting the interventional device of the invention into a body canal and positioning a proximal end-piece at one end of the body canal such as the kidney and a distal end-piece at the other end, such as the urinary bladder.

The foregoing and other objects, aspects, features, and advantages of the invention will become more apparent from the following description including drawings and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

"Distal" is used here to describe an end that is farther away from an origin of attachment. For a device that is at least partly implanted in a patient's body, its distal end is the end closest to an orifice on the patient's body through which the device enters, while its proximal end is the end deepest inside the patient's body.

The device of the invention is designed to maintain the patency of a body canal while simultaneously minimizing contact with the lining of the canal and preserving the anatomy of the canal. To that end, a common feature of each of the embodiments of the invention described herein is a plurality of interconnected loop-like elements that form a flexible, elongated body portion for insertion into the body canal. These loop elements each resembles a closed or nearly closed figure. Each loop is made of a member curved or doubled over defining at least an opening. And each separate loop member passes through at least one opening of another loop, forming a plurality of interconnected loops out of discrete loop members. Besides the interconnected loops, the elongated body portion of the device of the invention may also include one or more non-loop segments. The interventional device of the invention further includes a proximal end-piece and a distal end-piece, both of which may serve as a retention device.

For the elongated body portion of the interventional device of the invention, one source of flexibility arises from connections between loops where one loop connects with an adjacent loop at one of a variety of angles, allowing the elongated body portion to be reduced or extended to various pre-determined lengths. The other source of flexibility of the elongated body portion is the radial compressibility of the material used to manufacture individual loops. A delivery system for introducing the interventional device according to the invention is also provided herewith.

Figure 1:
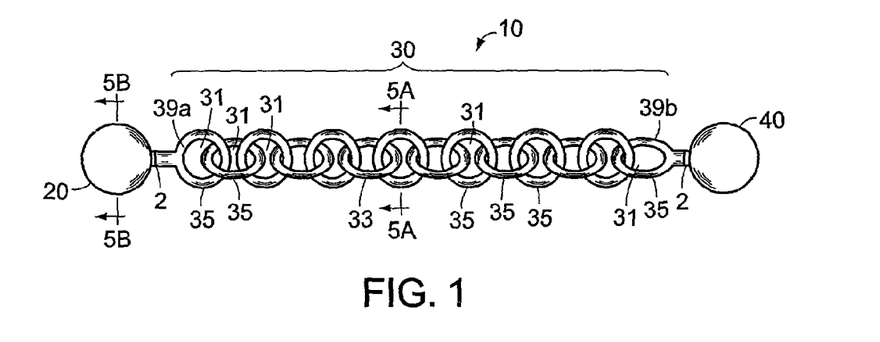
FIG. 1 is a schematic view of an embodiment of an interventional device according to the invention.

Referring to FIG. 1, device 10 generally includes a proximal end-piece 20, a distal end-piece 40, and an elongated body portion 30. The proximal end-piece 20 and the distal end-piece 40 may serve as retention devices to hold the proximal and distal ends of the device 10 at a specific anatomical location. For example, a specific anatomical location includes but is not limited to the renal pelvis, urinary bladder, or a blood vessel. Each end-piece 20, 40 is depicted as an embodiment having a substantially spherical shape in FIGS. 1 and 2, however, the shape of the end-pieces 20, 40 include other embodiments known to the skilled artisan and are not limited to those illustrated.

Referring still to FIG. 1, in an embodiment according to the invention, the body portion 30 includes a plurality of interconnected loops 33, which collectively resemble a chain. The length of the elongated body portion 30 is determined by the length of the body canal in which the interventional device 10 is to be inserted. For example, for positioning in the ureter of a patient, the length of the elongated body portion 30 of the interventional device 10, while varied from patient to patient, is typically about 14-20 inches, preferably about 16-18 inches. Each individual loop 33 includes a loop member 35 that defines at least one opening 31. The loop member 35 passes through at least one opening 31 of an adjacent loop 33 to make a connection between the two loops. The outside diameter of the loops 33 is determined by the inside diameter of the body canal into which the interventional device 10 is inserted. For example, for the ureter, the outside diameter of the loops 33 may be from about 0.026 inches to about 0.263 inches, and preferably from about 0.039 inches to about 0.197 inches.

In a particular embodiment according to the invention shown in FIG. 1, a plurality of loops 33 is interconnected in a linear fashion. In this embodiment, each loop member 35 of each loop 33 passes through one or two loop openings 31. The loop member 35 of a proximal end loop 39a, illustrated in FIG. 1, passes through the loop opening 31 of one adjacent loop 33 and is joined to a proximal end-piece 20. The loop member 35 of the distal end loop 39b passes through the loop opening 31 of an adjacent loop 33 and is joined to a distal end-piece 40. Each of the loop members 35 between the proximal end loop 39a and the distal end loop 39b passes through the openings of two other loops. The proximal end-piece 20 and the distal end-piece 40 are each joined to the adjacent loop member 35 by soldering, welding, adhesive or by other means known to the skilled artisan.

Figure 2:
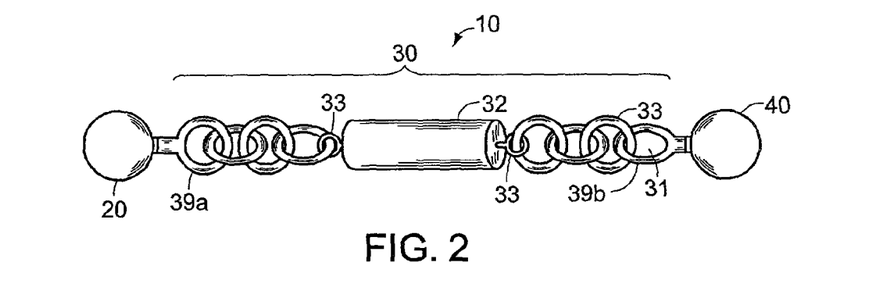
FIG. 2 is a schematic view of another embodiment of an interventional device according to the invention.

Referring now to FIG. 2, the elongated body portion 30 may include at least one non-loop segment 32 that is connected to at least one of the loops 33. The non-loop segment 32 may be any shape, such as a tubular segment or a spiral segment, and is not limited to the shape illustrated in FIG. 2. The non-loop segment 32 may be joined to the rest of the body portion 30 through a variety of connections. In a particular embodiment shown in FIG. 2, each end of the non-loop element 32 is joined to a loop 33. The loop 33 is in turn interconnected to other loops 33 in the elongated body portion 30. The non-loop segment 32 may be disposed at either end of the body portion 30 or anywhere between the ends of the body portion 30.

Figure 3A:
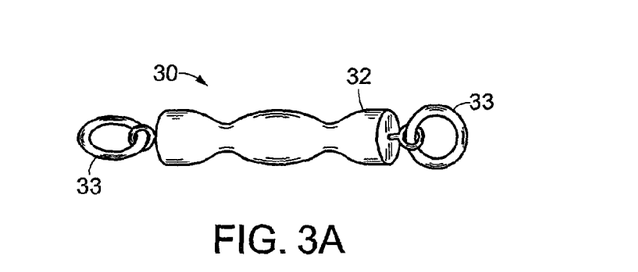
FIGS. 3A and 3B illustrate various embodiments of non-loop segments in the body portion of a device according to the invention.
Figure 3B:
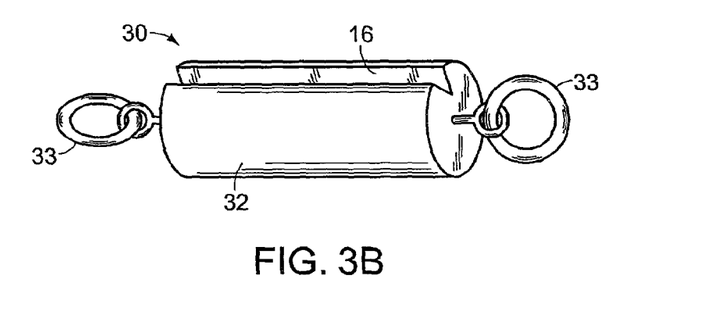

The non-loop segment 32 in the elongated body portion 30 of the device of the invention may have a contoured or uneven surface. These surfaces are designed to prevent stenosis and to help maintain a passage for fluid. In one embodiment, referring to FIG. 3A, the body portion of the non-loop segment 32 has an undulated surface. In another embodiment, referring to FIG. 3B, the surface of the non-loop segment 32 includes a longitudinal groove 16. In yet another embodiment, the element 32 is made of a compressible material that allows some adjustment in its diameter.

Figure 4A:
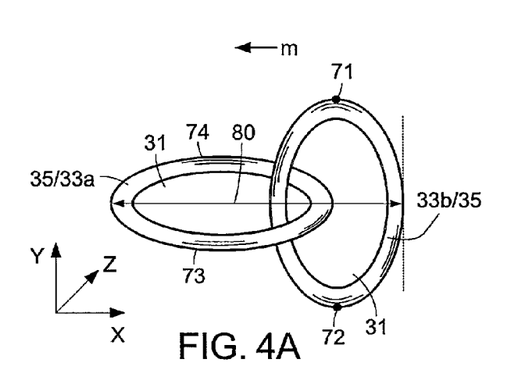
FIGS. 4A-4G illustrate various embodiments of the loops according to the invention.
Figure 4B:
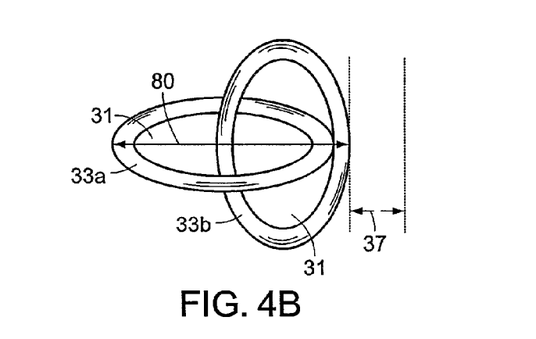
Figure 4C:
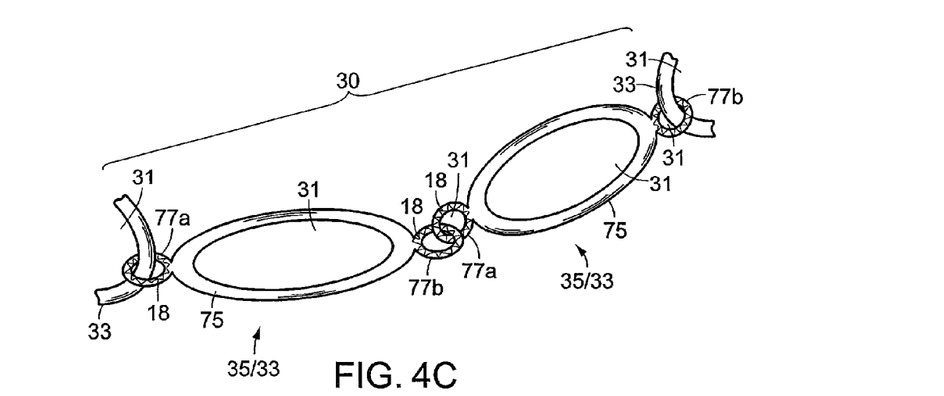
Figure 4D:
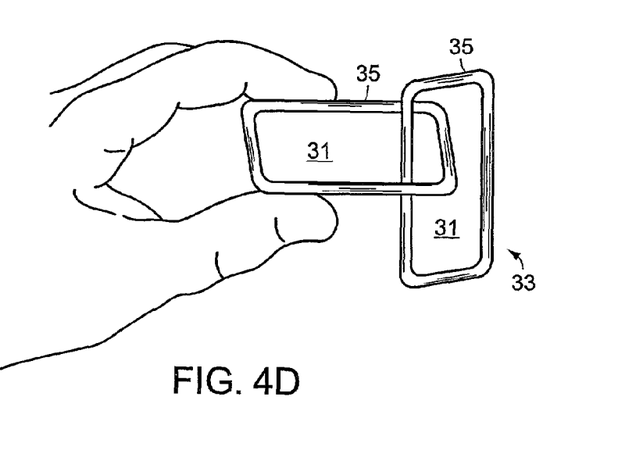

Referring now to FIGS. 4A-4I, the loops 33 and loop members 35 of the elongated body portion 30 can be of any shape that helps maintain the patency of a body canal. For example, the loops 33 can be substantially oval as illustrated, for example, in FIG. 4A, or substantially circular as illustrated, for example, in FIG. 4E, or substantially rectangular, for example, as illustrated in FIG. 4D. Having multiple, discrete but interconnected loops 33 in the body portion 30 is advantageous over known devices because it minimizes mucosal contact between the interventional device 10 and the lining of the body canal in which the device 10 is placed while simultaneously holding the body canal open to allow fluid to pass around the device 10.

In another embodiment, the loop member 35 may define more than one opening. For example, referring to FIG. 4C, the loop member 35 may define three openings 31 that are arranged parallel to the longitudinal axis of the body portion 30. In this embodiment, loop members 35 includes a middle ring 75 flanked by a first side ring 77a and a second side ring 77b opposite the first side ring 77a. In this particular embodiment, each of the side rings 77a, 77b passes through an opening 31 of an adjacent loop 33.

Figure 4E:
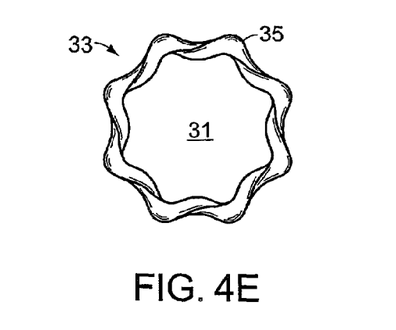
Figure 4F:
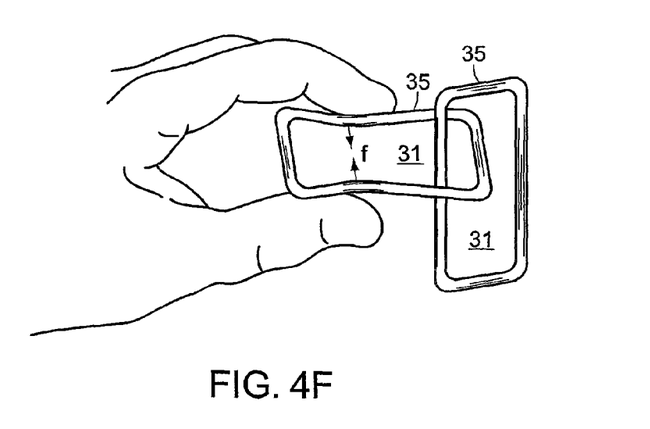
Figure 4G:
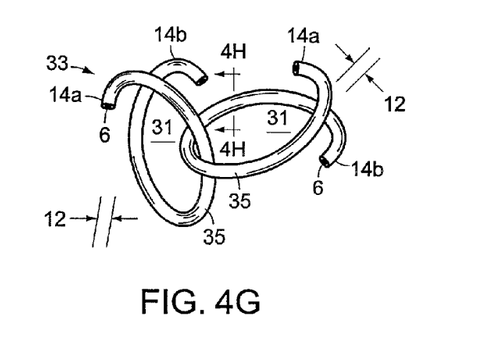
Figure 4H:
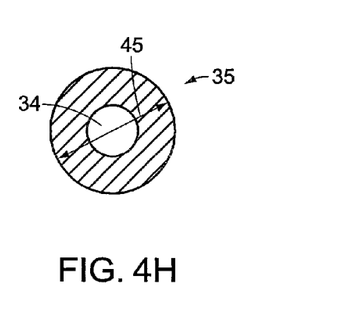
FIG. 4H illustrates a cross-sectional view of a loop member of the device of FIG. 4G taken at line "4H-4H."

In one embodiment according to the invention, the loop member 35 may be closed, i.e., loop member 35 has no ends, for example, as shown in FIG. 4A. In an alternate embodiment, referring to FIGS. 4G and 4H, the loop member 35 may be open with two unconnected ends 14a and 14b. A gap 12 is located between the two ends 14a and 14b. The width of the gap 12 indicated in FIG. 4G is less than the diameter 45 of the adjacent loop member 35 indicated in FIG. 4H, so that the adjacent loop member 35 will not dislodge from the loop 33.

The loop member 35 in accordance with the invention may be made by, for example, bending a cylindrical length of material into a closed or nearly closed figure. In one embodiment, the cylindrical material itself may be twisted about its longitudinal axis, for example, as shown in FIG. 4E. The cylindrical piece may be solid, which will give it a substantially circular cross section as shown in, for example, FIG. 2. Or the cylindrical piece 35 may be hollow, including one or more lumens 34, as illustrated in cross section in FIG. 4H. Materials used to manufacture the loop members 35 include, but are not limited to, nickel-titanium, polyurethane (e.g., Tecoflex® material), Flexima™ material, Perculflex® material, C-Flex® material, and silicone, for example.

According to the invention, each loop 33 moves in the opening 31 of an adjacent loop 33 constrained only by the cross-sectional diameter of each loop member 35 and the diameter of the loop openings 31.

Referring again to FIG. 4A, two adjacent loops 33 are shown in more detail. In this embodiment, one loop 33 moves in a direction along the X, Y, or Z axis or a combination of any of the three axes within the confines of the opening 31 of an adjacent loop 33. That is, the loop 33 forms a flexible connection with the adjacent loop 33 and can move in a plurality of axes. By having multiple flexible connections from loop to loop along the length of the body portion 30, the body portion 30 can conform to the contour of a body canal. The larger the number of flexible connections per unit length of the elongated body portion 30, the greater the flexibility of the elongated body portion 30. Thus, for a more tortuous body canal, a larger number of flexible connections is desirable. Also, by having numerous flexible connections in the body portion 30, the body portion of the device 10 is automatically adjustable to changes in the shape of the body canal during normal bodily activities, such as during urination.

An advantage of using a chain-like configuration for the body portion 30 is the volume of space that is generated between loops 33 for the passage of fluid. Referring still to FIG. 4A, a left loop 33a is shown to lie in an X-Z plane while a right loop 33b lies in an X-Y plane. The two farthest points in the Y direction on the right loop 33b are points 71 and 72 while the entire left loop 33a lies in a plane orthogonal to the Y-axis. The two adjacent loops 33a and 33b do not have to be orthogonal to each other. As long as the loops 33a, 33b are not in the same plane, space is available between the loops 33a, 33b for fluid passage. This feature according to the invention is an important advantage over conventional tubular stents because tissue ingrowth and stenosis may occur after operation is performed on the lining of the body canal. The chain-like body portion of the device 10 according to the invention, minimizes the chance that fluid passage will be completely blocked by tissue ingrowth and sterosis.

Referring again to FIGS. 4A and 4B, according to one embodiment of the invention, the loop 33b, moves within the opening of an adjacent loop 33a, when the loop 33b, shown in FIG. 4A, experiences a force in the direction denoted by arrow "m." The combined axial length 80 of the two loops 33a, 33b may be reduced by as much as a distance 37 shown in FIG. 4B. Therefore, when multiple loops 33 are linked together, the combined axial length 80 of the body portion 30 becomes adjustable. Because the combined axial length 80 of the body portion 30 is adjustable, it is easier for the interventional device 10 to fit into a body canal of a particular length. Moreover, the adjustability in the combined axial length 80 of the elongated body portion 30 allows the interventional device 10 to automatically adjust to changes in the length of the body canal that occur spontaneously, for example, when a patient moves from a sitting to a standing position. This feature of the interventional device 10 provides greater comfort to the patient.

Figure 5A:
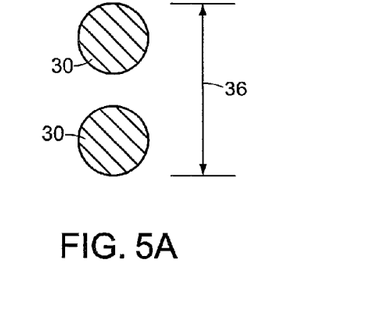
FIG. 5A illustrates a cross-sectional view of the body portion of the device of FIG. 1 taken at line "5A-5A."
Figure 5B:
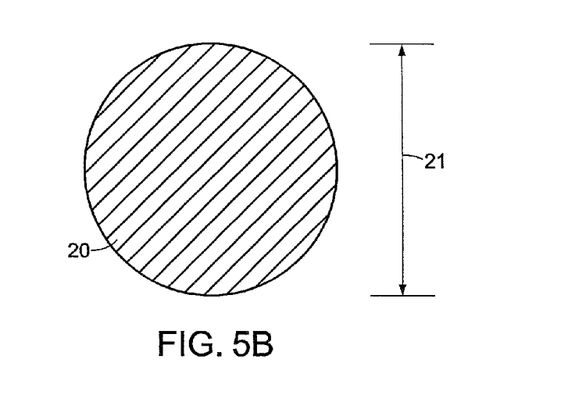
FIG. 5B illustrates a cross-sectional view of the proximal end-piece of the device of FIG. 1 taken at line "5B-5B."

Referring again to FIG. 1, in one embodiment of the invention, the end-pieces 20 and 40 of the interventional device 10 of the invention may serve as a retention device at their respective end. In one embodiment according to the invention, the cross-section of end-pieces 20, 40 have larger area than the cross-section of body portion 30. For example, a cross-section of the body portion 30 taken at the line "5A-5A" in FIG. 1 is shown in FIG. 5A, and a cross section of the proximal piece 20 taken at line "5B-5B" in FIG. 1 is shown in FIG. 5B. The cross-sectional diameter 21 of the proximal piece 20 is greater than the cross-sectional diameter 36 of the body portion 30.

Figure 6A:
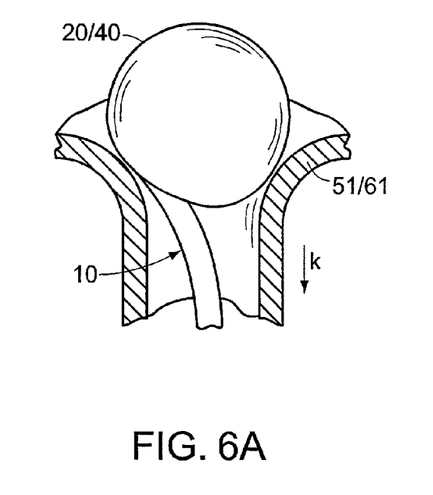
FIGS. 6A-6D illustrate various embodiments of the end-piece of the interventional device according to the invention.
Figure 6B:
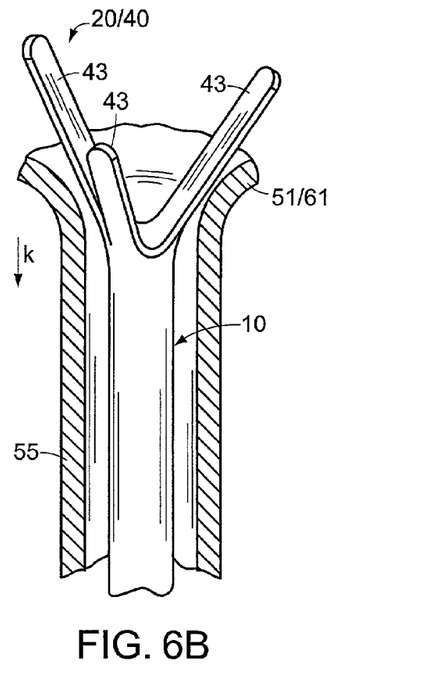
Figure 6C:
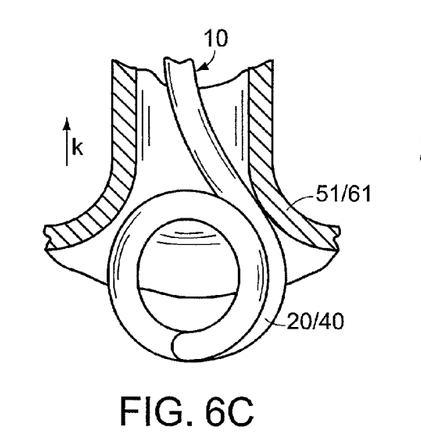
Figure 6D:
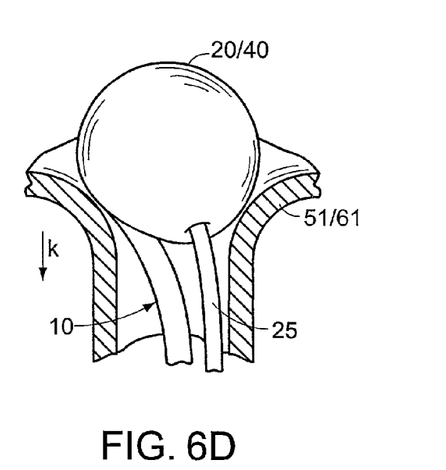

FIGS. 6A-6D illustrate embodiments of the end-pieces 20, 40. Referring now to FIG. 6A, in one embodiment, either the proximal end-piece 20 or the distal end-piece 40, is substantially spherical. In one embodiment illustrated in FIG. 6B, the end-piece 20 or end-piece 40, has three arms 43 that extend outward from the center of the elongated body portion 30 to stop migration of the device 10 in the direction indicated by the arrow "k." In another embodiment, the end-piece 20 or the end-piece 40, is a coil as shown in FIG. 6C. In the embodiment shown in FIG. 6D, the end-piece 20 or the end-piece 40 may be an inflatable balloon connected to a source of fluid through an infusion channel 25. The inflatable balloon can be inflated or deflated through the infusion channel 25.

Figure 7:
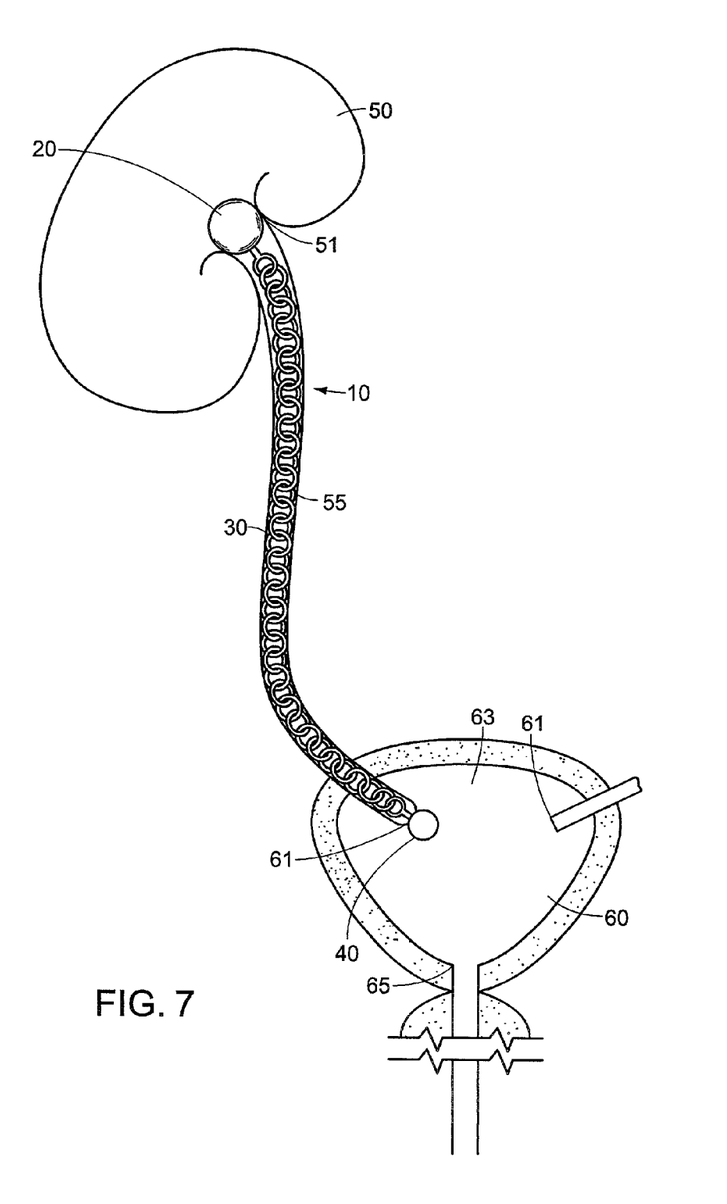
FIG. 7 illustrates an embodiment of the invention positioned in the lumen of the ureter of a patient.

Either end-piece 20 or end-piece 40 may be positioned at an anatomical location such as the renal pelvis 51 or the ureteral orifice 61, illustrated in FIG. 7. Because the diameter of the end-piece 20, 40 is designed to be larger than that of the body canal, the end-piece 20, 40 will prevent device 10 from migrating in the direction "k" shown in FIGS. 6A-6D.

The device 10 according to the invention is made of a bio-compatible material. In one embodiment, according to the invention, all or portions of the device 10 may be made, for example, of a compressible material, such as a metal alloy (e.g., nickel-titanium) or a polymeric material (e.g., polyurethane). Additional suitable materials for the device 10 include Flexima™ material, Perculflex® material, C-Flex® material, and silicone.

Referring again to FIGS. 4D and 4F, in a particular embodiment, the member 35 of loops 33 of the body portion 30 of the device 10 may be made of a compressible material that, when squeezed, deforms at least in one direction indicated by arrow "f." The material composition of the loop member 35 lends flexibility so that the device 10 is more likely to conform to the anatomy of the patient's body canal and lessens patient discomfort. Of course, it is not necessary that such compressible material be used, other materials, such as non-compressible metal, can also be used. In a particular embodiment, the device of the invention is made of a biodegradable material, and would not require removal from the patient.

Referring again to FIG. 1, in a particular embodiment according to the invention, the interventional device 10 may contain one or more conventional radiopaque markers 2 to aid in more precise positioning of the device 10 in a patient's body canal. In a particular embodiment, the markers 2 are placed near the proximal end-piece 20 and the distal end-piece 40 to indicate their positions. The radiopaque markers 2 can be, for example, a metal ring or barium sulfide embedded in the device 10, or the marker 2 may be a band of radiopaque ink painted on portions of the device 10. Alternatively, the entire device 10 or the entire body portion 30 may be made of a radiopaque material.

Figure 4I:
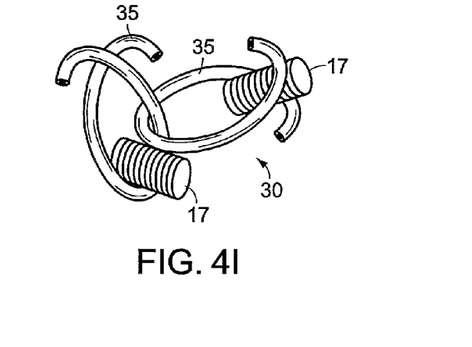
FIG. 4I illustrates the device of FIG. 4G with drug-releasing plugs or discs.

Referring again to FIG. 4I, the interventional device 10 according to the invention may further contain a drug-dispenser 17 for releasing a drug into the body. Drugs that may be dispensed by the drug dispenser 17 may include antimicrobial or anti-inflammatory reagents to prevent infection and/or inflammation of the body canal where the interventional device 10 is placed. Referring to FIG. 4I, for example, the drug-dispenser 17 may be a drug-containing plug or disk disposed within the body portion 30 of the interventional device 10. In this case, the drug-dispenser 17 is disposed within loop members 35 of the body portion 30 of the interventional device 10. In a hollow loop member 35, illustrated in FIG. 4H, for example, the drug-containing substance may be disposed inside the lumen 34 and dispensed through a lumen aperture 6 on the member 35, such as the aperture 6 illustrated in FIG. 4G.

Referring again to FIG. 4C, in another embodiment according to the invention, a drug-releasing coating 18 is deposited on portions of the device, for example, on side rings 77a and 77b of the loops 33. In a particular embodiment, the coating 18 releases the drug in a time-controlled fashion. The coating 18 may include a porous layer containing antibiotics such as ciprofloxacin and a rate-limiting overlayer that results in a constant, sustained release (C. Kwok et al, Journal of Controlled Release 62 (1999) 301-311). Such coating may include an antibiotic-containing hydrogel (J. Pugach et al, Journal of Urology (1999), v. 162, 883-887). Other examples of such coating may be found in U.S. Pat. Nos. 5,902,283 and 5,520,664, the entire disclosure of both incorporated by reference herein.

FIG. 7 illustrates a method for using the device of the invention in a patient to treat a patient's body canal 55, for example, the ureter. A ureter 55 normally directs urine from a kidney 50 into the urinary bladder 60. The ureter 55 extends from the kidney 50 at renal pelvis 51 to the urinary bladder 60 at ureteral orifice 61. The bladder neck 65 funnels urine into the urethra. The triangulated area between the two ureteral orifices 61 and the bladder neck 65 is the trigone area 63. Once the device of the invention 10 is positioned within the ureter 55, as described below, the device 10 maintains patency of the ureter 55 for passage of urine between the renal pelvis 51 and the urinary bladder 60.

In an embodiment of the invention for placing and using the device 10 in the body canal, such as the ureter of the patient, the operator uses a trans-urethal approach and uses a guidewire and a cystoscope to aid in placement of the interventional device 10 in the ureter. As illustrated in FIG. 7, the proximal end-piece 20 is positioned in the renal pelvis 51 and the distal end-piece 40 is positioned in the lumen of the urinary bladder 60. The elongated body portion 30 extends from the distal end-piece 40 in the urinary bladder 60, through the intramural canal of the urinary bladder wall and the lumen of the ureter 55 to the proximal end-piece 20 in the renal pelvis 51. Following positioning of the interventional device 10 in the ureter 55, the operator withdraws the guidewire. The interventional device 10 of the invention may be also placed in a body canal via other means such as a transcutaneous means, known to one skilled in the art.

Still referring to FIG. 7, the interconnected loops 33 of the body portion 30 maintain patency of the ureter 55 for urine passage. In addition, the body portion 30 contacts the lining of the ureter 55 only focally compared to more conventional tubular prostheses that have full contact with the ureteral lining. Further, the flexible connection between loops 33 in the elongated body portion 30 permits the interventional device 10 to readily conform to the anatomy of the ureter 55, even during ureteral movements. With the tortuous path of the ureter 55 kept largely intact in the presence of the elongated body portion 30, vesico-ureteral reflux, which occurs primarily during voiding, can be prevented because it is more difficult for fluid to reflex up the ureter 55 when the tortuous path of the ureter 55 is maintained.

Still referring to FIG. 7, the device 10 may be retained at the renal pelvis 51 by the proximal end-piece 20. It may be additionally retained at the ureteral orifice 61, by the distal end-piece 40. Having an end-piece on both ends prevents the device 10 from migrating, minimizing mucosal irritation and pain stemming from the sliding of body portion 30 within the ureter 55 and minimizing contact between the device 10 and the sensitive trigone area 63 of the urinary bladder 60. Moreover, the flexible connection between the loops 33 also allows automatic adjustment in the length of the body portion 30, which helps to adapt the interventional device 10 to ureters 55 of different lengths or to changes in the length of the ureter during bodily functions.

Figure 8:
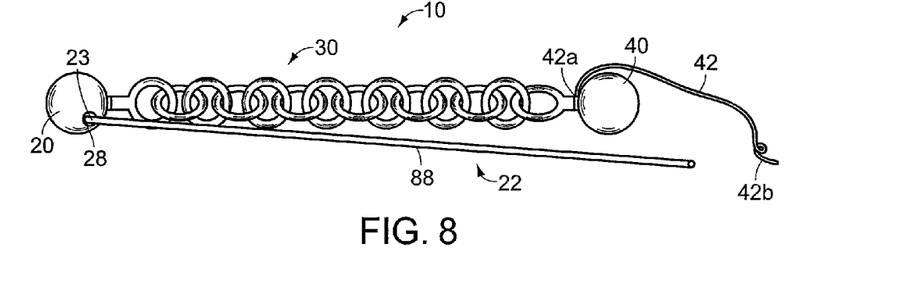
FIG. 8 illustrates an embodiment of the device with a delivery assembly.

In another embodiment according to the invention, referring to FIG. 8, a delivery assembly 22, for example, a stylet 88, is associated with the proximal end-piece 20. A retrieval suture 42, may also be associated with the distal end-piece 40, which may aid in the removal of the device 10 from the body canal. The retrieval suture 42 may be a thread, a ribbon, a wire, a tape, a suture, or the like. The retrieval suture 42 is attached by its proximal end 42a by means known to the skilled artisan, and the distal end 42b is free. The distal free end 42b may be grasped by the operator to withdraw the interventional device 10 from the body canal.

Still referring to FIG. 8, in a particular embodiment of the delivery assembly 22, a stiff stylet 88 is reversibly attachable to the proximal end-piece 20 at an opening 28 in the proximal end-piece 20. The stylet 88 has sufficient column strength so that, once attached to the proximal end-piece 20, the stylet 88 can be pushed up a body canal 55, advancing the rest of the interventional device 10 along with it. The material used to manufacture the stylet 88 is flexible so that the flexibility of the interventional device 10 being delivered is not substantially compromised. Suitable materials for the stylet 88 include but are not limited to C-Flex® materials, or Flexima™ material. In a particular embodiment, the stylet 88 is associated with the device 10 only at the proximal end-piece 20, and is free of the body portion 30 and the distal end-piece 40.

Figure 9A:
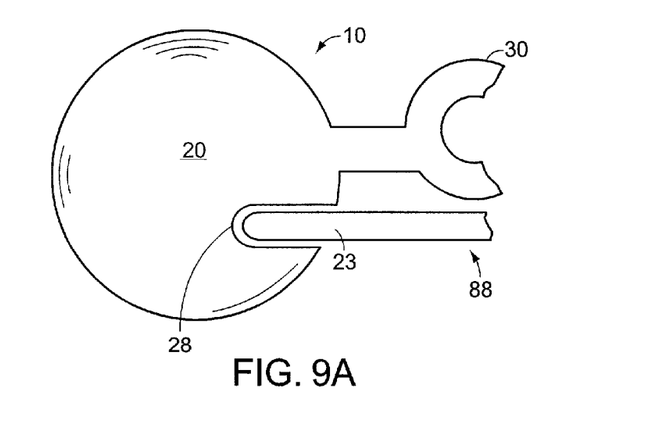
FIG. 9A illustrates an embodiment of a delivery assembly according to the invention.

Referring now to FIG. 9A, in an embodiment according to the invention, the proximal end 23 of the stylet 88 fits into an opening 28 in the proximal end-piece 20, allowing an operator to use the stylet 88 to push the device 10 up the body canal 55. Once the device 10 is placed properly in the body canal 55, the proximal end 23 of the stylet 88 can be pulled out of the opening 28 in the reverse direction as the style 88 is withdrawn from the body canal 55.

Figure 9B:
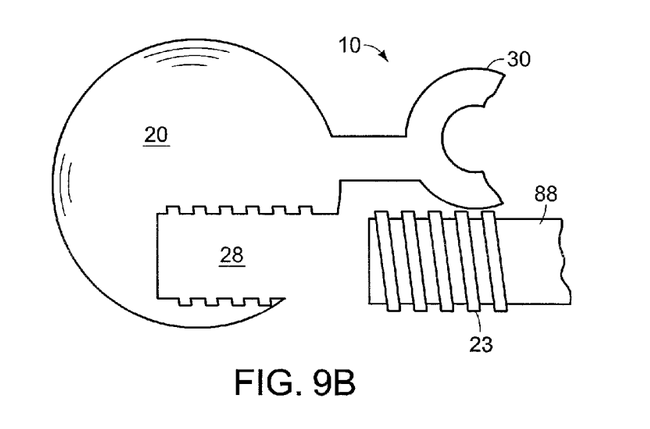
FIG. 9B illustrates another embodiment of a delivery assembly reversibly attachable to the interventional device according to the invention, with the delivery assembly detached from the interventional device.
Figure 9C:
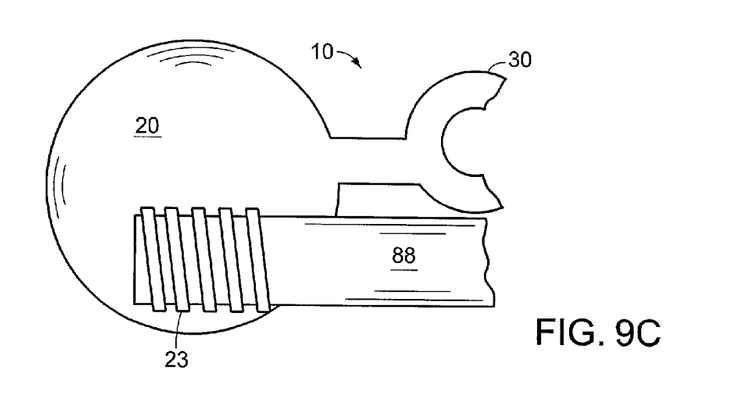
FIG. 9C illustrates the delivery assembly of FIG. 9B with it being attached to the interventional device.

Referring to FIGS. 9B-9C, in another embodiment according to the invention, the proximal end 23 of the stylet 88 is a male luer portion having spiral threads that fit into a complementary female luer portion of the opening 28 of the proximal end-piece 20. The male luer portion 23 is seated in the female luer portion 28 by twisting the stylet 88 in one direction. Once the interventional device 10 is placed properly in the body canal 55, turning the stylet 88 in the reverse direction will detach the style 88 from the proximal end-piece 20.

Figure 9D:
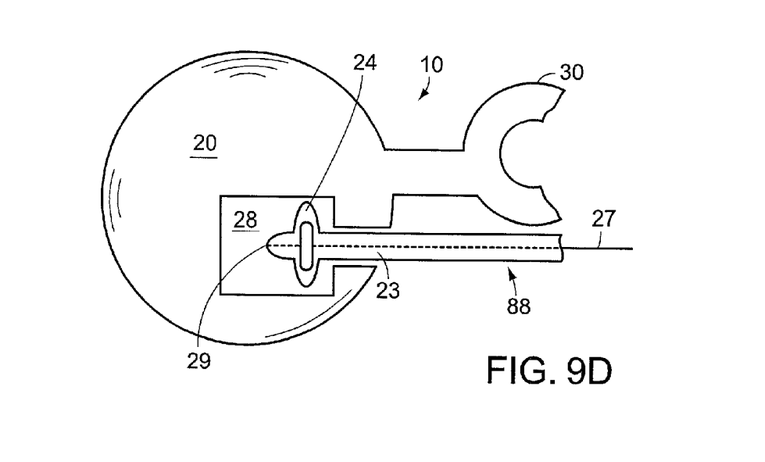
FIG. 9D illustrates another alternate embodiment of a delivery assembly reversibly attachable to the interventional device according to the invention, with the delivery assembly detached from the interventional device.
Figure 9E:
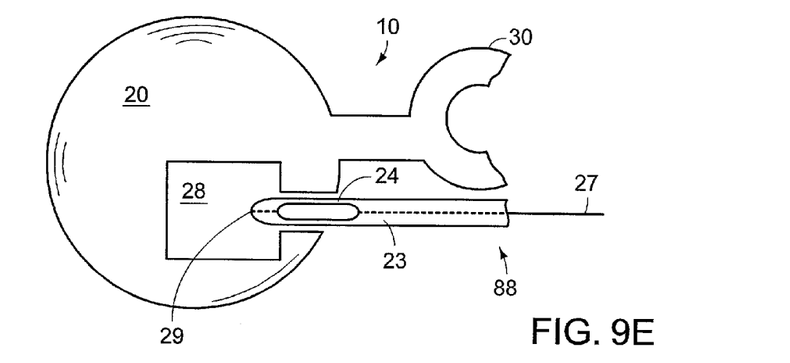
FIG. 9E illustrates the delivery assembly of FIG. 9C with it being attached to the interventional device.

In another alternate embodiment according to the invention, illustrated in FIGS. 9D and 9E, the proximal end 23 of the stylet 88 comprises a malecot. A spring-tensioned wire 27 is connected to a proximal tip 29 of the stylet 88. Actuating the wire 27 by pulling the wire 27 in the distal direction will cause the arms 24 of the malecot to extend laterally, seating the proximal end 23 of the stylet 88 in the opening 28 and preventing the proximal end 23 from slipping out. Releasing the wire 27 collapses the arms 24 of the malecot 23 and enables the operator to detach the stylet 88 from the proximal end-piece 20 and to withdraw the stylet 88 from the device 10.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A device for treating a body canal, comprising:
a medical device that includes:
a proximal end-piece positioned at a proximal-most end of said medical device, a first portion of the proximal end-piece defining an opening configured to receive at least a portion of an insertion device;
a distal end-piece positioned at a distal end of said medical device, the end-pieces being spheres; and
an elongated body portion disposed between said proximal end-piece and said distal end-piece, said body portion comprising a plurality of interconnected loops directly connected to a second potion of the proximal end-piece and to the distal end-piece and configured to fit within said body canal, each of said loops comprising a member defining at least one opening, the member of each loop passing through at least one opening of another loop to form said plurality of interconnected loops, and wherein the elongated body portion further comprises a substantially cylindrical non-loop segment having a distal end surface and a proximal end surface, the distal end surface being directly connected to a first loop of the interconnected loops and the proximal end surface being directly connected to a second loop of said interconnected loops, wherein the non-loop segment is a single continuous structure, a diameter of at least one of the end-pieces being larger than a diameter of any component of the elongated body; the substantially cylindrical non-loop segment having an undulating outer surface extending from a distal end of the substantially cylindrical non-loop segment to a proximal end of the substantially cylindrical non-loop segment.

2. The device of claim 1 wherein said plurality of interconnected loops comprises discrete loops.

3. The device of claim 1 wherein at least one of said loops is substantially oval.

4. The device of claim 1 wherein at least one of said loops is substantially circular.

5. The device of claim 1 wherein at least one of said loops is substantially rectangular.

6. The device of claim 1 wherein said member of at least one of said loops comprises a substantially circular cross-section.

7. The device of claim 1 wherein at least one of said members defines a closed loop.

8. The device of claim 1 wherein at least one of said members defines an open loop comprising two ends.

9. The device of claim 8 further comprising a gap between said open loop ends, the largest dimension of said gap being no greater than the diameter of an adjacent loop member.

10. The device of claim 1 wherein at least one of said members is hollow.

11. The device of claim 1 wherein said members are biodegradable.

12. The device of claim 1 further comprising a drug releasable from said device.

13. The device of claim 12, further comprising a plug for releasing said drug.

14. The of claim 12 wherein said device further comprises a coating disposed on at least a portion of said device, said coating releasing said drug in a solution.

15. The device of claim 1, wherein at least one of said end-pieces comprises a cross-sectional area larger than a cross-sectional area of said body portion.

16. The device of claim 1, wherein the substantially cylindrical non-loop segment defines a longitudinal axis, a radial center of the substantially cylindrical non-loop segment extends along the longitudinal axis, the first loop of the interconnected loops and the second loop of the interconnected loops extend along the longitudinal axis.

17. The device of claim 1, wherein the medical device includes a removal member extending from a portion of the medical device.

18. A device for treating a body canal, comprising:
a medical device that includes:
a proximal end-piece positioned at a proximal-most end of said medical device, a first portion of the proximal end-piece defining an opening configured to receive at least a portion of an insertion device;
a distal end-piece positioned at a distal-most end of said medical device; and
an elongated body portion disposed between said proximal end-piece and said distal end piece, said body portion comprising a plurality of interconnected loops directly connected to a second portion of the proximal end-piece and to the distal end-piece and configured to fit within said body canal, each of said loops comprising a member defining at least one opening, the member of each loop passing through at least one opening of another loop to form said plurality of interconnected loops, the elongated body portion further comprising a substantially cylindrical non-loop segment having a proximal end surface and a distal end surface, the proximal end surface being directly connected to a first loop of the interconnected loops and the distal end surface being directly connected to a second loop of said interconnected loops, wherein the non-loop segment is a single continuous structure, a diameter of at least one of the end-pieces being larger than a diameter of any component of the elongated body, and the end pieces being spherical in shape; the substantially cylindrical non-loop segment having an undulating outer surface extending from a distal end of the substantially cylindrical non loop segment to a proximal end of the substantially cylindrical non-loop segment.

19. The device of claim 18, wherein at least one of the end-pieces is configured to hold a respective end of the device at a specific anatomical location.

20. The device of claim 19, wherein the specific anatomical location includes one of a renal pelvis, a urinary bladder, or a blood vessel.

21. The device of claim 18, further including a proximal loop member joined to the proximal end-piece and a distal loop member joined to the distal end-piece.

22. The device of claim 21, wherein the proximal loop member and the distal loop member are joined to the proximal end-piece and the distal end-piece, respectively, by one of welding, soldering, or adhesive.

23. The device of claim 18 wherein said member of at least one of said loops comprises a substantially circular cross-section.

24. The device of claim 18 wherein at least one of said members comprises a closed loop.

25. The device of claim 18, wherein the non-loop segment is made of a compressible material.

26. The device of claim 18, wherein the substantially cylindrical non-loop segment defines a longitudinal axis, a radial center of the substantially cylindrical non-loop segment extends along the longitudinal axis, the first loop of the interconnected loops and the second loop of the interconnected loops extend along the longitudinal axis.

27. The device of claim 18, wherein the medical device includes a removal member extending from a portion of the medical device.

28. A device for treating a body canal, comprising:
a medical device that includes:
a proximal end-piece positioned at a proximal-most end of said medical device, a first portion of the proximal end-piece defining an opening configured to receive at least a portion of an insertion device;
a distal end-piece positioned at a distal end of said medical device, the end-pieces having a spherical shape; and
an elongated body portion disposed between said proximal end-piece and said distal end-piece, said body portion comprising a plurality of interconnected loops directly connected to a second portion of the proximal end-piece and to the distal end-piece and configured to fit within said body canal, each of said loops comprising a member defining at least one opening, the member of each loop passing through at least one opening of an adjacent loop to form said plurality of interconnected loops, the elongate body portion further comprising a substantially cylindrical non-loop segment comprising a first end directly connected to a first loop of the interconnected loops and a second end directly connected to a second loop of said interconnected loops, wherein the non-loop segment is a single continuous structure, a diameter of at least one of the end-pieces being larger than a diameter of any component of the elongated body, and wherein adjacent interconnected loops are moveable along each of an X, Y, and Z orthogonal axis relative to each other at least during deployment of the medical device in the body canal, the substantially cylindrical non-loop segment defines a longitudinal axis, a radial center of the substantially cylindrical non-loop segment extends along the longitudinal axis, the first loop of the interconnected loops and the second loop of the interconnected loops extend along the longitudinal axis; the substantially cylindrical non-loop segment having an undulating outer surface extending from a distal end of the substantially cylindrical non-loop segment to a proximal end of the substantially cylindrical non-loop segment.

29. The device of claim 28, wherein each of the plurality of interconnected loops is configured to move within the confines of the opening of an adjacent loop.

30. The device of claim 28, wherein the interconnected loops are configured to permit fluid to pass through each at least one opening.

31. The device of claim 28, wherein an axial length of the body portion is adjustable.

32. The device of claim 28 wherein said member of at least one of said loops comprises a substantially circular cross-section.

33. The device of claim 28 wherein at least one of said members comprises a closed loop.

34. The device of claim 28, wherein the medical device includes a removal member extending from a portion of the medical device.

35. A device for treating a body canal, comprising:
a medical device that includes:
a proximal end-piece positioned at a proximal-most end of said medical device, a first portion of the proximal end-piece defining an opening configured to receive at least a portion of an insertion device;
a distal end-piece positioned at a distal-most end of said medical device, the end-pieces being spherical in shape; and
an elongated body portion disposed between said proximal end-piece and said distal end-piece, said body portion comprising a plurality of interconnected loops directly connected to a second portion of the proximal end-piece and to the distal end-piece and configured to fit within said body canal, each of said loops comprising a member defining at least one opening, the member of each loop passing through at least one opening of another loop to form said plurality of interconnected loops, and wherein the elongated body portion further comprises a non-loop segment having a distal end surface and a proximal end surface, the distal end surface being directly connected to a first loop of the interconnected loops and the proximal end surface being directly connected to a second loop of said interconnected loops, wherein the non-loop segment is a single continuous structure, a cross-sectional diameter of at least one of the end-pieces being greater than a cross-sectional diameter of any component of the elongated body; the non-loop segment having an undulating outer surface extending from a distal end of the non-loop segment to a proximal end of the non-loop segment.

36. The device of claim 35 wherein the member of at least one of said loops comprises a substantially circular cross-section.

37. The device of claim 35 wherein at least one of the members comprises a closed loop.

38. The device of claim 35, wherein the non-loop segment defines a longitudinal axis, a radial center of the non-loop segment extends along the longitudinal axis, the first loop of the interconnected loops and the second loop of the interconnected loops extend along the longitudinal axis.

39. The device of claim 35, wherein the medical device includes a removal member extending from a portion of the medical device.

40. A device for treating a body canal, comprising:
a medical device that includes:
a proximal end-piece positioned at a proximal end of said medical device, a first portion of the proximal end-piece defining an opening configured to receive at least a portion of an insertion device, the proximal end-piece being spherical;
a distal end-piece positioned at a distal end of said medical device, the distal end-piece being spherical; and
an elongated body portion disposed between said proximal end-piece and said distal end-piece, said body portion comprising a plurality of interconnected loops directly connected to a second portion of the proximal end-piece and to the distal end-piece and configured to fit within said body canal, each of said loops comprising a member defining at least one opening, the member of each loop being biodegradable and passing through at least one opening of another loop to form said plurality of interconnected loops, and wherein the elongated body portion further comprises a substantially cylindrical non-loop segment connected to at least one of said interconnected loops comprising a first end directly connected to a first loop of the interconnected loops and a second end directly connected to a second loop of said interconnected loops, wherein the non-loop segment is a single continuous structure, a diameter of at least one of the end-pieces being larger than a diameter of any component of the elongated body, the substantially cylindrical non-loop segment defines a longitudinal axis, a radial center of the substantially cylindrical non-loop segment extends along the longitudinal axis, the first loop of the interconnected loops and the second loop of the interconnected loops extend along the longitudinal axis; the substantially cylindrical non-loop segment having an undulating outer surface extending from a distal end of the substantially cylindrical non-loop segment to a proximal end of the substantially cylindrical non-loop segment.

41. The device of claim 40, wherein the medical device includes a removal member extending from a portion of the medical device.

42. A device for treating a body canal, comprising:
a medical device that includes:
a proximal end-piece positioned at a proximal-most end of said medical device, a first portion of the proximal end-piece defining an opening configured to receive at least a portion of an insertion device;
a distal end-piece positioned at a distal end of said medical device, the end-pieces having a spherical shape; and
an elongated body portion disposed between said proximal end-piece and said distal end-piece, said body portion comprising a plurality of interconnected loops directly connected to a second portion of the proximal end-piece and to the distal end-piece and configured to fit within said body canal, each of said loops comprising a member defining at least one opening, the member of each loop passing through at least one opening of another loop to form said plurality of interconnected loops, and wherein the elongated body portion further comprises a substantially cylindrical non-loop segment made of a compressible material and connected to at least one of said interconnected loops comprising a first end directly connected to a first loop of the interconnected loops and a second end directly connected to a second loop of said interconnected loops, wherein the non-loop segment is a single continuous structure, a diameter of at least one of the end-pieces being larger than a diameter of any component of the elongated body, the substantially cylindrical non-loop segment defines a longitudinal axis, a radial center of the substantially cylindrical non-loop segment extends along the longitudinal axis, the first loop of the interconnected loops and the second loop of the interconnected loops extend along the longitudinal axis; the substantially cylindrical non-loop segment having an undulating outer surface extending from a distal end of the substantially cylindrical non-loop segment to a proximal end of the substantially cylindrical non-loop segment.

43. The device of claim 42, wherein the medical device includes a removal member extending from a portion of the medical device.

44. A device for treating a body canal, comprising:
a medical device that includes:
a proximal end-piece positioned at a proximal-most end of said medical device, a first portion of the proximal end-piece defining an opening configured to receive at least a portion of an insertion device;
a distal end-piece positioned at a distal end of said medical device, the end-pieces having a spherical shape; and
an elongated body portion disposed between said proximal end-piece and said distal end-piece, said body portion comprising a plurality of interconnected loops directly connected to a second portion of the proximal end-piece and the to distal end-piece and configured to fit within said body canal, each of said loops comprising a member defining at least one opening, the member of each loop passing through at least one opening of an adjacent loop to form said plurality of interconnected loops, the elongate body portion further comprising a substantially cylindrical non-loop segment made of a compressible material and comprising a proximal end surface and a distal end surface, the distal end surface being directly connected to a first loop of the interconnected loops and the proximal end surface being directly connected to a second loop of said interconnected loops, wherein the non-loop segment is a single continuous structure, a diameter of at least one of the end-pieces being larger than a diameter of any component of the elongated body, and wherein adjacent interconnected loops are moveable along each of an X, Y, and Z orthogonal axis relative to each other at least during deployment of the medical device in the body canal; the non-loop segment having an undulating outer surface extending from a distal end of the non-loop segment to a proximal end of the non-loop segment.

45. The device of claim 44, wherein the substantially cylindrical non-loop segment defines a longitudinal axis, a radial center of the substantially cylindrical non-loop segment extends along the longitudinal axis, the first loop of the interconnected loops and the second loop of the interconnected loops extend along the longitudinal axis.

46. The device of claim 44, wherein the medical device includes a removal member extending from a portion of the medical device.

47. A device for treating a body canal, comprising:
a medical device that includes:
a proximal end-piece positioned at a proximal-most end of said medical device, a first portion of the proximal end-piece defining an opening configured to receive at least a portion of an insertion device;
a distal end-piece positioned at a distal end of said medical device, the end-pieces being spheres; and
an elongated body portion disposed between said proximal end-piece and said distal end-piece, said body portion comprising a plurality of interconnected loops directly connected to a second portion of the proximal end-piece and to the distal end-piece and configured to fit within said body canal, each of said loops comprising a member defining at least one opening, the member of each loop being biodegradable and passing through at least one opening of another loop to form said plurality of interconnected loops, and wherein the elongated body portion further comprises a substantially cylindrical non-loop segment connected to at least one of said interconnected loops comprising a first end directly connected to a first loop of the interconnected loops and a second end directly connected to a second loop of said interconnected loops, wherein the non-loop segment is a single continuous structure, a diameter of at least one of the end-pieces being larger than a diameter of any component of the elongated body, the substantially cylindrical non-loop segment defines a longitudinal axis, a radial center of the substantially cylindrical non-loop segment extends along the longitudinal axis, the first loop of the interconnected loops and the second loop of the interconnected loops extend along the longitudinal axis; the substantially cylindrical non-loop segment having an undulating outer surface extending from a distal end of the substantially cylindrical non-loop segment to a proximal end of the substantially cylindrical non-loop segment.

48. The device of claim 47, wherein the medical device includes a removal member extending from a portion of the medical device.

* * * * *